US008716454B2

(12) United States Patent
Kullmann et al.

(10) Patent No.: US 8,716,454 B2
(45) Date of Patent: May 6, 2014

(54) SOLID COMPOSITIONS

(75) Inventors: Simon Kullmann, Neustadt an der Weinstrasse (DE); Ulrich Westedt, Schriesheim (DE); Mirko Pauli, Ludwigshafen (DE); Rudolf Schroeder, Worms-Pfeddersheim (DE); Gerd Woehrle, Eppelheim (DE); Tanja Heitermann, Wiesloch (DE); Renato Koenig, Hassloch (DE); Madlen Thiel, Schifferstadt (DE); Yi Gao, Vernon Hills, IL (US); Jianwei Wu, Libertyville, IL (US); Bryan K. Erickson, Pleasant Prairie, WI (US)

(73) Assignee: Abbvie Inc., North Chicago, IL (US)

( * ) Notice: Subject to any disclaimer, the term of this patent is extended or adjusted under 35 U.S.C. 154(b) by 254 days.

(21) Appl. No.: 13/156,793

(22) Filed: Jun. 9, 2011

(65) Prior Publication Data

US 2012/0264780 A1    Oct. 18, 2012

Related U.S. Application Data

(63) Continuation-in-part of application No. 12/813,301, filed on Jun. 10, 2010.

(60) Provisional application No. 61/186,291, filed on Jun. 11, 2009, provisional application No. 61/242,836, filed on Sep. 16, 2009, provisional application No. 61/243,596, filed on Sep. 18, 2009.

(51) Int. Cl.
*C07K 16/00* (2006.01)
*A61K 38/00* (2006.01)

(52) U.S. Cl.
USPC ........ 530/388.8; 530/389.4; 514/3.7; 514/4.3

(58) Field of Classification Search
None
See application file for complete search history.

(56) References Cited

U.S. PATENT DOCUMENTS

| | | | |
|---|---|---|---|
| 5,830,867 A | 11/1998 | Bhatnagar et al. |
| 5,935,982 A | 8/1999 | Dykstra et al. |
| 6,235,493 B1 | 5/2001 | Bissell et al. |
| 6,369,091 B1 | 4/2002 | Sircar et al. |
| 6,703,403 B2 | 3/2004 | Norbeck et al. |
| 6,919,366 B2 | 7/2005 | Sircar et al. |
| 7,141,574 B2 | 11/2006 | Beaulieu et al. |
| 7,659,270 B2 | 2/2010 | Bachand et al. |
| 7,704,992 B2 | 4/2010 | Bachand et al. |
| 7,728,027 B2 | 6/2010 | Pack et al. |
| 7,741,347 B2 | 6/2010 | Bachand et al. |
| 7,745,636 B2 | 6/2010 | Bachand et al. |
| 7,759,495 B2 | 7/2010 | Bachand et al. |
| 7,763,731 B2 | 7/2010 | Rockway et al. |
| 7,906,655 B2 | 3/2011 | Belema et al. |
| 8,101,643 B2 | 1/2012 | Qiu et al. |
| 2003/0004203 A1 | 1/2003 | Sircar et al. |
| 2003/0100582 A1 | 5/2003 | Sircar et al. |
| 2005/0075343 A1 | 4/2005 | Sircar et al. |
| 2005/0197375 A1 | 9/2005 | Sircar et al. |
| 2006/0003942 A1 | 1/2006 | Tung et al. |
| 2006/0058317 A1 | 3/2006 | Gravestock et al. |
| 2006/0105997 A1 | 5/2006 | Arrington et al. |
| 2007/0004741 A1 | 1/2007 | Apodaca et al. |
| 2007/0142434 A1 | 6/2007 | Sandanayaka et al. |
| 2007/0197558 A1 | 8/2007 | Betebenner et al. |
| 2007/0232627 A1 | 10/2007 | Betebenner et al. |
| 2007/0299068 A1 | 12/2007 | Karp et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0075696 A1 | 3/2008 | Parsons et al. |
| 2008/0221107 A1 | 9/2008 | Giordanetto et al. |
| 2008/0299075 A1 | 12/2008 | Bachand et al. |
| 2008/0311075 A1 | 12/2008 | Bachand et al. |
| 2009/0004111 A1 | 1/2009 | Rice et al. |
| 2009/0041716 A1 | 2/2009 | Kim et al. |
| 2009/0043107 A1 | 2/2009 | Pack et al. |
| 2009/0068140 A1 | 3/2009 | Bachand et al. |
| 2009/0093456 A1 | 4/2009 | Arnold et al. |
| 2009/0104151 A1 | 4/2009 | Hanson et al. |
| 2009/0202478 A1 | 8/2009 | Bachand et al. |
| 2009/0202483 A1 | 8/2009 | Bachand et al. |
| 2010/0055071 A1 | 3/2010 | Leivers et al. |
| 2010/0068176 A1 | 3/2010 | Belema et al. |

(Continued)

FOREIGN PATENT DOCUMENTS

BR    PI0401908 A    1/2006
DE    75755 C    6/1984

(Continued)

OTHER PUBLICATIONS

Adjabeng G., et al., "Novel Class of Tertiary Phosphine Ligands Based on a Phospha-adamantane Framework and use in the Suzuki cross-Coupling Reactions of Aryl Halides Under Mild Conditions," Organic Letters, 2003, vol. 5 (6), pp. 953-955.
Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69 (15), pp. 5082-5086.
Aldous D.J., et al. , "A Simple Enantioselective Preparation of (2S,5S)-2,5-diphenylpyrrolidine and Related Diaryl Amines," Tetrahedron Asymmetry, 2000, vol. 11, pp. 2455-2462.
Alesso E.N., et al., "Synthesis of Diastereoisomeric 1,2,3-Triphenylindans," Australian Journal of Chemistry, 1997, vol. 50, pp. 149-152.
Angiolini M., et al., "Synthesis of Azabicycloalkane Amino Acid Scaffolds as Reverse-Turn Inducer Dipeptide Mimics ," European Journal Organization Chemistry, 2000, pp. 2571-2581.

(Continued)

Primary Examiner — James H Alstrum Acevedo
Assistant Examiner — Jeanette Lieb
(74) Attorney, Agent, or Firm — Xu Zhang; Abbvie Inc.

(57) ABSTRACT

The present invention features solid compositions comprising Compound $I_A$, $I_B$ or $I_C$, or a pharmaceutically acceptable salt thereof, in an amorphous form. In one embodiment, Compound $I_A$, $I_B$ or $I_C$, or a pharmaceutically acceptable salt thereof, is formulated in an amorphous solid dispersion which comprises a pharmaceutically acceptable hydrophilic polymer and preferably a pharmaceutically acceptable surfactant.

22 Claims, No Drawings

(56) References Cited

U.S. PATENT DOCUMENTS

| | | |
|---|---|---|
| 2010/0080772 A1 | 4/2010 | Belema et al. |
| 2010/0143499 A1 | 6/2010 | Condon |
| 2010/0158862 A1 | 6/2010 | Kim et al. |
| 2010/0160355 A1 | 6/2010 | Degoey et al. |
| 2010/0168138 A1 | 7/2010 | Degoey et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1 | 10/2010 | Donner et al. |
| 2010/0303755 A1 | 12/2010 | Lopez et al. |
| 2010/0310512 A1 | 12/2010 | Guo et al. |
| 2010/0316607 A1 | 12/2010 | Or et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | Degoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0189129 A1 | 8/2011 | Qiu et al. |
| 2011/0195044 A1 | 8/2011 | Romine |
| 2011/0207699 A1 | 8/2011 | Degoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2012/0004196 A1 | 1/2012 | Degoey et al. |
| 2012/0028978 A1 | 2/2012 | Zhong et al. |
| 2012/0040977 A1 | 2/2012 | Li et al. |

FOREIGN PATENT DOCUMENTS

| | | |
|---|---|---|
| EP | 2242751 A1 | 10/2010 |
| JP | 2003282270 A | 10/2003 |
| JP | 2007-320925 A * | 12/2007 |
| JP | 2010126571 A | 6/2010 |
| WO | WO9427627 A1 | 12/1994 |
| WO | WO9961020 A1 | 12/1999 |
| WO | WO0012521 A1 | 3/2000 |
| WO | WO03082186 A2 | 10/2003 |
| WO | WO2004005283 A1 | 1/2004 |
| WO | WO2004014313 A2 | 2/2004 |
| WO | WO2004014852 A2 | 2/2004 |
| WO | WO2004014852 A3 | 4/2004 |
| WO | WO2004014313 A3 | 12/2005 |
| WO | WO2006020951 A1 | 2/2006 |
| WO | WO2006033703 A1 | 3/2006 |
| WO | WO2006133326 A1 | 12/2006 |
| WO | WO2007070556 A2 | 6/2007 |
| WO | WO2007070600 A2 | 6/2007 |
| WO | WO2007076034 A2 | 7/2007 |
| WO | WO2007076035 A2 | 7/2007 |
| WO | WO2007082554 A1 | 7/2007 |
| WO | WO2007070556 A3 | 8/2007 |
| WO | WO2007081517 A8 | 9/2007 |
| WO | WO2007070600 A3 | 11/2007 |
| WO | WO2007131366 A1 | 11/2007 |
| WO | WO2007144174 A1 | 12/2007 |
| WO | WO2008014236 A1 | 1/2008 |
| WO | WO2008014238 A2 | 1/2008 |
| WO | WO2008021927 A2 | 2/2008 |
| WO | WO2008021928 A2 | 2/2008 |
| WO | WO2008021936 A2 | 2/2008 |
| WO | WO2008021928 A3 | 3/2008 |
| WO | WO2008021936 A3 | 4/2008 |
| WO | WO2008021927 A3 | 5/2008 |
| WO | WO2008064218 A2 | 5/2008 |
| WO | WO2008070447 A2 | 6/2008 |
| WO | WO2008074450 A2 | 6/2008 |
| WO | WO2008064218 A3 | 10/2008 |
| WO | WO2008128121 A1 | 10/2008 |
| WO | WO2008133753 A2 | 11/2008 |
| WO | WO2008144380 A1 | 11/2008 |
| WO | WO2009003009 A1 | 12/2008 |
| WO | WO2009020534 A2 | 2/2009 |
| WO | WO2009020825 A1 | 2/2009 |
| WO | WO2009020828 A1 | 2/2009 |
| WO | WO2008070447 A3 | 3/2009 |
| WO | WO2009093082 A1 | 7/2009 |
| WO | WO2009094224 A1 | 7/2009 |
| WO | WO2009102318 A1 | 8/2009 |
| WO | WO2009102325 A1 | 8/2009 |
| WO | WO2009102568 A1 | 8/2009 |
| WO | WO2009102633 A1 | 8/2009 |
| WO | WO2009102694 A1 | 8/2009 |
| WO | WO2009136290 A1 | 11/2009 |
| WO | WO2009143361 A1 | 11/2009 |
| WO | WO2009155709 A1 | 12/2009 |
| WO | WO2010015090 A1 | 2/2010 |
| WO | WO2010017401 A1 | 2/2010 |
| WO | WO2010039793 A1 | 4/2010 |
| WO | WO2010059858 A1 | 5/2010 |
| WO | WO2010062821 A1 | 6/2010 |
| WO | WO2010065668 A1 | 6/2010 |
| WO | WO2010065674 A1 | 6/2010 |
| WO | WO2010065681 A1 | 6/2010 |
| WO | WO2010075376 A2 | 7/2010 |
| WO | WO2010091413 A1 | 8/2010 |
| WO | WO2010096302 A1 | 8/2010 |
| WO | WO2010096462 A1 | 8/2010 |
| WO | WO2010096777 A1 | 8/2010 |
| WO | WO2010099527 A1 | 9/2010 |
| WO | WO2010111483 A1 | 9/2010 |
| WO | WO2010111534 A1 | 9/2010 |
| WO | WO2010111673 A1 | 9/2010 |
| WO | WO2010115767 A1 | 10/2010 |
| WO | WO2010117635 A1 | 10/2010 |
| WO | WO2010117704 A1 | 10/2010 |
| WO | WO2010117977 A1 | 10/2010 |
| WO | WO2010120621 A1 | 10/2010 |
| WO | WO2010120935 A1 | 10/2010 |
| WO | WO2010122162 A1 | 10/2010 |
| WO | WO2010132538 A1 | 11/2010 |
| WO | WO2010132601 A1 | 11/2010 |
| WO | WO2010138368 A1 | 12/2010 |
| WO | WO2010138488 A1 | 12/2010 |
| WO | WO2010138790 A1 | 12/2010 |
| WO | WO2010138791 A1 | 12/2010 |
| WO | WO2010144646 A2 | 12/2010 |
| WO | WO2010148006 A1 | 12/2010 |
| WO | WO2011004276 A1 | 1/2011 |
| WO | WO2011009084 A2 | 1/2011 |
| WO | WO2011015658 A1 | 2/2011 |
| WO | WO2011026920 A1 | 3/2011 |
| WO | WO2011028596 A1 | 3/2011 |
| WO | WO2011031904 A1 | 3/2011 |
| WO | WO2011031934 A1 | 3/2011 |
| WO | WO2011050146 A1 | 4/2011 |
| WO | WO2011054834 A1 | 5/2011 |
| WO | WO2011059850 A1 | 5/2011 |

(56) References Cited

FOREIGN PATENT DOCUMENTS

| WO | WO2011059887 A1 | 5/2011 |
|---|---|---|
| WO | WO2011060000 A1 | 5/2011 |
| WO | WO2011066241 A1 | 6/2011 |
| WO | WO2011068941 A2 | 6/2011 |
| WO | WO2011075439 A1 | 6/2011 |
| WO | WO2011075607 A1 | 6/2011 |
| WO | WO2011075615 A1 | 6/2011 |
| WO | WO2011079327 A1 | 6/2011 |
| WO | WO2011081918 A1 | 7/2011 |
| WO | WO2011082077 A1 | 7/2011 |
| WO | WO2011087740 A1 | 7/2011 |
| WO | WO2011091417 A1 | 7/2011 |
| WO | WO2011091446 A1 | 7/2011 |
| WO | WO2011091532 A1 | 8/2011 |
| WO | WO2011112429 A1 | 9/2011 |
| WO | WO2011119853 A1 | 9/2011 |
| WO | WO2011119858 A1 | 9/2011 |
| WO | WO2011119860 A1 | 9/2011 |
| WO | WO2011119870 A1 | 9/2011 |
| WO | WO2011127350 A1 | 10/2011 |
| WO | WO2011146401 A1 | 11/2011 |
| WO | WO2011150243 A1 | 12/2011 |
| WO | WO2011156543 A2 | 12/2011 |

OTHER PUBLICATIONS

Boehm T., et al., "Uber Die Bildung Von Gamma-Piperidonderivaten Aus Azetessigester, Aromatischen Aldehyden and Aminen, Eine Modifikation Der Hantzschschen Pyridinsynthese," Pharmaceutical,1943, vol. 281, pp. 62-77.
Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.
Bundgaard H., "Design of Pro Drugs," 1985, pp. 1-6.
Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Stucture-Activity Relationships," Journal of Medicinal Chemistry, 2008, vol. 51 (17), pp. 5243-5263.
Chong J.M., et al., "Asymmetric Synthesis of trans.2,5-Diphenylpyrrolidine: A C2-Symmetric Chirai Amine," Tetrahedron Asymmetry, 1995, vol. 6 (2), pp. 409-418.
Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1 (11), pp. 1839-1842.
Clarke P.A., et al., "Pot, Atom and Step Economic (Pase) Synthesis of Highly Functionalized Piperidines: A Five-Component Condensation," Tetrahedron Letters , 2007, vol. 48 , pp. 5209-5212.
Clarke P.A., et al., "Pot, Atom and Step Economic (PASE) Synthesis of Highly Substituted Piperidines:A Five-Component Condensation," Synthesis, 2008, No. 28, pp. 3530-3532.
Collado I., et al , "Stereoselective Addition of Grignard-Derived Organocopper Reagents to N-Acyliminium Ions: Synthesis of Enantiopure 5- and 4,5-Substituted Prolinates ," Journal of Organic Chemistry , 1995, vol. 60, pp. 5011-5015.
Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19 (6), pp. 1779-1783.
Dell'erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.
Effenberger F., et al., "Synthesis, Structure, and Spectral Behavior of Donor-Acceptor Substituted Biphenyls," The Journal of Organic Chemistry, 1983, vol. 48, pp. 4649-4658.
Fan X., et al., "An Efficient and Practical Synthesis of the HIV Protease Inhibitor Atazanavir via a Highly Diastereoselective Reduction Approach," Organic Process Research and Development, 2008, vol. 12 (1), pp. 69-75.

Fiedler., "Encyclopedia of Excipients for Pharmaceuticals, Cosmetics and related Areas," 5th Edition, Hoepfner E.M., et al., eds., Editio Cantor Verlag Aulendorf, 2002, Table of Contents.
Gordon T.D., et al , "Synthetic Approaches to the Azole Peptide Mimetics," Tetrahedron Letters, 1993, vol. 34(12), pp. 1901-1904.
Greene T.W., et al., "Protection for the Amino group," Protective Groups in Organic Synthesis, 1999, Third Edition, pp. 494-653.
Hartwig J.F., et al., "III.3.2 Palladium-Catalyzed Amination of Aryl Halides and Related Reactions," Handbook of Organopalladium Chemistry for Organic Synthesis, 2002, pp. 1051-1096.
Hoover J.E, Remington's Pharmaceutical Sciences, 15th Edition, 1975, Table of Contents.
International Preliminary Report on Patentability and Written Opinion for the Application No. PCT/US2010/031102, mailed on Oct. 18, 2011, 7 pages.
International Search Report and Written Opinion for Application No. PCT/US2009/038077, mailed on Jan. 21, 2011, 16 pages.
International Search Report and Written Opinion for Application No. PCT/US2009/069177, mailed on Aug. 10, 2010, 17 pages.
International Search Report for Application No. PCT/US2009/069188, mailed on Jun. 8, 2010, 4 pages.
International Search Report for the Application No. PCT/US2010/031102, mailed on Sep. 1, 2010, 4 pages.
Jacques et al., "Enantiomers, Racemates, and Resolutions," J. Wiley & Sons, Chapter 3, pp. 197-213, 1981.
Jeffrey J.L., et al., "Concise Synthesis of Pauciflorol F Using a Larock Annulation," Organic Letters, 2009, vol. 11 (23), pp. 5450-5453.
Jing Q., et al., "Bulky Achiral Triarylphosphines Mimic BINAP in Ru(II)—Catalyzed Asymmetric Hydrogenation of Ketones," Advanced Synthesis & Catalysis, 2005, vol. 347, pp. 1193-1197.
Khan A.T., et al., "Effects of Substituents in the-"Position of 1,3-Dicarbonyl Compounds in Bromodimethylsulfonium Bromide-Catalyzed Multicomponet Reactions: A Facile Access to Functionalized Piperidines," Journal of organic chemistry, 2008, vol. 73 , pp. 8398-8402.
Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67 (17), pp. 5993-6000.
Li Chuan-Ying., et al., "Olefination of Ketenes for the Enantioselective Synthesis of Allenes via an Ylide Route," Tetrahedron, 2007, vol. 63, pp. 8046-8053.
Lieberman L., et al., eds., Pharmaceutical Dosage Forms, vol. 1, Marcel Dekker, Inc., 1980, Table of Contents.
Louie J., et al., "Palladium-Catalyzed Amination of Aryl Triflates and Importance of Triflate Addition Rate," Journal of Organic Chemistry, 1997, vol. 62 (5), pp. 1268-1273.
L-selectride, Retrieved from the Internet<URL: http://en.wikipedia.org/w/index.php?oldid=488453454>.
Lucas S., et al.,"In Vivo Active Aldosterone Synthase Inhibitors with Improved Aelectivity: Lead Optimization Providing a Series of Pyridine Substituted 3,4-Dihydro-1H-Quinolin-2-one Derivatives," Journal of Medicinal Chemistry, 2008, vol. 51 (24), pp. 8077-8087.
Masters K., "Spray Drying Handbook" 4th Edition, John Wiley & Sons, 1985, Table of Contents.
Masui M., et al., "A Practical Method for Asymmetric Borane Reduction of Prochiral Ketones Using Chiral Amino Alcohols and Trimethyl Borate," Synlett, 1997, pp. 273-274.
Matzeit A., et al., "Radical Tandem Cyclizations by Anodic Decarboxylation of Carboxylic Acids," Synthesis, 1995, pp. 1432-1444.
Misra M., et al., "Organocatalyzed Highly Atom Economic One Pot Synthesis of Tetrahydropyridines as Antimalarials," Bioorganic & Medicinal Chemistry, 2009, vol. 17 , pp. 625-633.
Moinet C., et al., "Novel Non-Peptide Ligands for the Somatostatin sst3 Receptor," Bioorganic & Medicinal Chemistry Letters, 2001, vol. 11 (8), pp. 991-995.
Muci A.R., et al., "Practical Palladium Catalysts for C-N and C-O Bond Formation," Topics in Current Chemistry, 2002, vol. 219, pp. 131-209.

(56) References Cited

OTHER PUBLICATIONS

Muri E.M.F., et al., "Pseudo-Peptides Derived From Isomannide as Potential Inhibitors of Serine Proteases," Amino Acids, 2005, vol. 28 (4), pp. 413-419.
Naylor E.M., et al., "3-Pyridylethanolamines: Potent and Selective Human 63 Adrenergic Receptor Agonists," Bioorganic & Medicinal Chemistry Letters, 1998, vol. 8 (21), pp. 3087-3092.
Nevar N. M., et al., "One Step Preparation of 1,4-Diketones from Methyl Ketones and a-Bromomethyl Ketones in the Presence of ZnCl2•t-BuOH•Et2NR as a Condensation Agent," Synthesis, 2000, vol. 9, pp. 1259-1262.
Pak V.D., et al., "Catalytic Condensation of Schiff's Base With P-Methoxybenzal Acetone," Catalytic Synthesis of Organic Nitrate Compounds, 1970, vol. 68 (Part 4), pp. 66-71.
Peng T., et al., "Construction of a Library of Rhodol Fluorophores for Developing New Fluorescent Probes," Organic Letters, 2010, vol. 12 (3), pp. 496-499.
Penning T.D., et al, "Discovery and SAR of 2-(1-Propylpiperidin-4-yl)-1H-Benzimidalole-4-Carboxamide: A Potent Inhibitor of Poly(ADP-ribose) Polymerase (PARP) for the Treatment of Cancer ," Bioorganic & Medicinal Chemistry, 2008, vol. 16(14), pp. 6965-6975.
Polymer Handbook, Brandrup J., et al., Eds., Interscience Publishers, 1975, Table of Contents, III-139-III-192.
Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19 (3), pp. 414-419.
Sato M., et al., "Efficient Preparation of Optically Pure C2-Symmetrical Cyclic Amines for Chiral Auxiliary," Synthesis, 2004, vol. 9, pp. 1434-1438.
Sawyer J.S., et al., "Synthetic and Structure/Activity Studies on Acid-Substituted 2-Arylphenols:Discovery of 2-[2-Propyl-3-[3-[2-ethyl-4-(4-fluorophenyl)-5-hydroxyphenoxy]-propoxy]phenoxy] benzoic Acid, a High-Affinity Leukotriene B4 Receptor Antagonist," Journal of Medicinal Chemistry, 1995, vol. 38 (22), pp. 4411-4432.
Smith A.B., et al., "Indole Diterpene Synthetic Studies: Development of a Second-Generation Synthetic Strategy for (+)-Nodulisporic Acids A and B," Journal of Organic Chemistry, 2007, vol. 72 (13), pp. 4611-4620.
Smith D.C., et al., "Reissert Compound Chemistry. XXVI. The Syntheses of Bis-Benzylisoquinolines," Journal of Heterocyclic Chemistry, 1976, vol. 13, pp. 573-576.
Sperling L. H., "Introduction to Physical Polymer Science," 2nd Edition, John Wiley & Sons, Inc., 1992, Table of Contents.
Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119 (49), pp. 11986-11987.
Takagi S., et al., "Antimicrobial Agents From Bletilla Striata," Phyrochemisrry, 1983, vol. 22 (4), pp. 1011-1015.
Tatsumi K., et al., "Enzyme-Mediated Coupling of 3,4-Dichloroaniline and Ferulic Acid: A Model for Pollutant Binding to Humic Materials," Environmental Science & Technology, 1994, vol. 28 , pp. 210-215.
Tellinghuisen T.L., et al., "Structure of the Zinc-Binding Domain of an Essential Component of the Hepatitis C Virus Replicase," Nature, 2005, vol. 435 (7040), pp. 374-379.
Vallee R.J., et al., "Photoannelation Reactions of 3-(Alk-1-ynyl)cyclohept-2-en-1-ones," Helvetica Chimica Acta, 2010, vol. 93 (1), pp. 17-24.
Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49 (2), pp. 269-276.
Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.
Wolfe J.P., et al., "Palladium-Catalyzed Amination of Aryl Triflates," Journal of Organic Chemistry, 1997, vol. 62 (5), pp. 1264-1267.
Xiao D., et al., "A Practical Synthetic Pathway to Polysubstituted Tetrahydropyridines via Multicomponent Reactions Catalyzed by BF3•OEt2," Synlett, 2005, vol. 10, pp. 1531-1534.
Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Journal of the American Chemical Society , 2002, vol. 4 (23), pp. 4029-4032.

\* cited by examiner

SOLID COMPOSITIONS

The present application is a continuation-in-part of U.S. patent application Ser. No. 12/813,301, filed Jun. 10, 2010, which claims the benefit from U.S. Provisional Application Ser. No. 61/186,291, filed Jun. 11, 2009, U.S. Provisional Application Ser. No. 61/242,836, filed Sep. 16, 2009, and U.S. Provisional Application Ser. No. 61/243,596, filed Sep. 18, 2009. All of these applications are incorporated herein by reference in their entireties.

FIELD OF THE INVENTION

The present invention relates to solid compositions comprising anti-HCV compounds and methods of using the same to treat HCV infection.

BACKGROUND

The hepatitis C virus (HCV) is an RNA virus belonging to the Hepacivirus genus in the Flaviviridae family. The enveloped HCV virion contains a positive stranded RNA genome encoding all known virus-specific proteins in a single, uninterrupted, open reading frame. The open reading frame comprises approximately 9500 nucleotides and encodes a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects, and viral elimination from the body is often inadequate. Therefore, there is a need for new drugs to treat HCV infection.

SUMMARY OF THE INVENTION

The present invention features solid compositions comprising a HCV inhibiting compound or a pharmaceutically acceptable salt thereof, wherein said HCV inhibiting compound is selected from the group consisting of:

methyl[(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]-1H-pyrrol-2-yl}phenyl)-1H-imidazol-2-yl]pyrrolidin-1-yl}-3-methyl-1-oxobutan-2-yl]carbamate

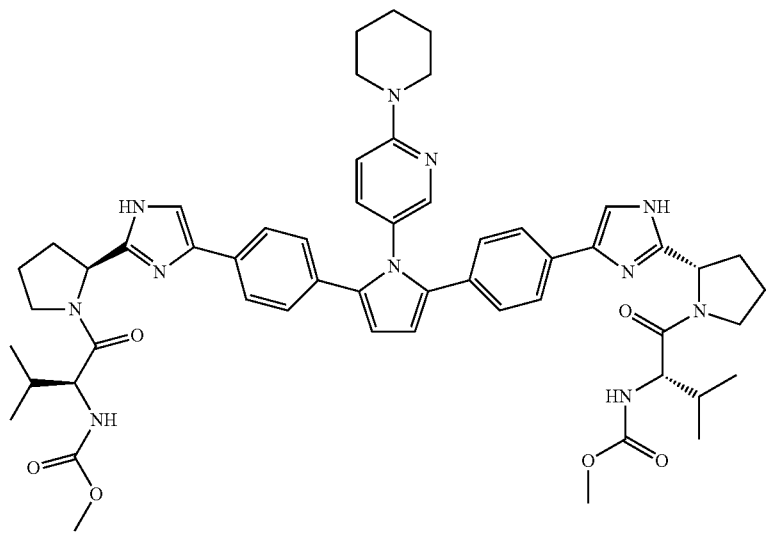

(, hereinafter Compound I$_A$), methyl{(2S,3R)-1-[(2S)-2-{6-[(2R,5R)-1-(4-tert-bu-tylphenyl)-5-(2-{(2S)-1-[N-(methoxycarbonyl)-O-methyl-L-threonyl]pyrrolidin-2-yl}-1H-benzimidazol-6-yl)pyrroli-din-2-yl]-1H-benzimidazol-2-yl}pyrrolidin-1-yl]-3-methoxy-1-oxobutan-2-yl}carbamate

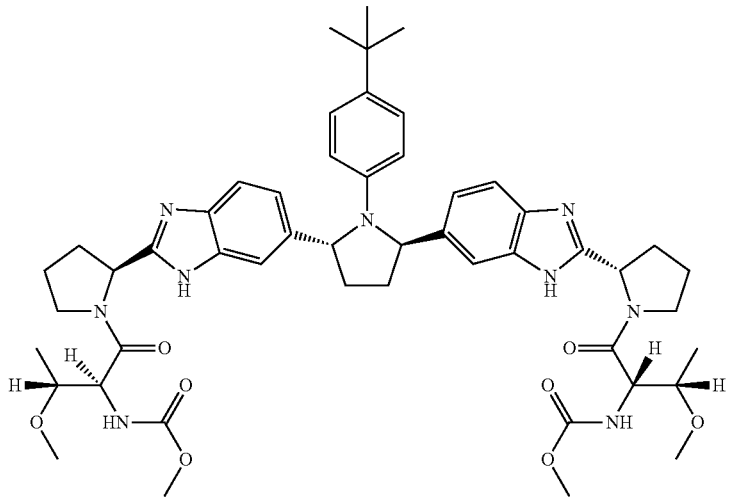

(                                                               , hereinafter Compound I$_B$), and
methyl{(2S)-1-[(2S)-2-{5-[(2R,5R)-1-[2,5-difluoro-4-(trifluoromethyl)phenyl]-5-{2-[(2S)-1-{(2S)-2-[(methoxy-carbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate

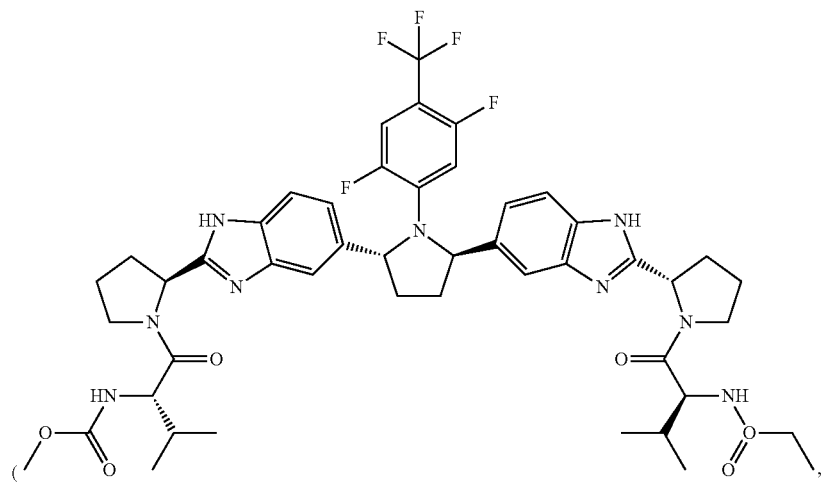

(                                                               , hereinafter Compound I$_C$).

Compound I$_A$, I$_B$ and I$_C$ are potent HCV inhibitors. The solid compositions of the invention comprise (1) a compound selected from Compound I$_A$, I$_B$ or I$_C$, or a pharmaceutically acceptable salt thereof, in an amorphous form, (2) a pharmaceutically acceptable hydrophilic polymer, and optionally (3) a pharmaceutically acceptable surfactant.

In one aspect, the present invention features a solid composition comprising a solid dispersion, wherein the solid dispersion comprises (1) a compound selected from Compound I$_A$, I$_B$ or I$_C$ (or a pharmaceutically acceptable salt thereof) in an amorphous form, (2) a pharmaceutically acceptable hydrophilic polymer, and (3) a pharmaceutically acceptable surfactant. The surfactant can be, without limitation, either formulated in the solid dispersion or separately combined or mixed with the solid dispersion. Preferably, the hydrophilic polymer has a T$_g$ of at least 50° C. More preferably, the hydrophilic polymer has a T$_g$ of at least 80° C. Highly preferably, the hydrophilic polymer has a T$_g$ of at least 100° C. Also preferably, the surfactant has a HLB value of at least 10. Hydrophilic polymers with T$_g$s of below 50° C., such as a polymer having a T$_g$ of at least 25° C., and/or surfactants having HLB values of below 10, can also be used.

In one embodiment of this aspect of the invention, the hydrophilic polymer is selected from homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, or polysaccharide. Non-limiting examples of suitable hydrophilic polymers include homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, graft copolymer of polyethylene glycol/polyvinyl caprolactam/polyvinyl acetate (e.g., Soluplus), polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, or xanthan gum, or a combination thereof. In some cases, sugar alcohols can be used in addition to, or in lieu of, hydrophilic polymers.

In another embodiment of this aspect of the invention, the surfactant is selected from polyoxyethylene castor oil derivates, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, or sorbitan fatty acid mono ester. Non-limiting examples of suitable surfactants include polyoxyethyleneglycerol triricinoleate or polyoxyl 35 castor oil (Cremophor EL; BASF Corp.) or polyoxyethyleneglycerol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60), mono fatty acid ester of polyoxyethylene sorbitan, such as mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40) or polyoxyethylene (20) sorbitan monolaurate (Tween 20), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate (e.g., lauroglycol FCC), D-alpha-tocopheryl polyethylene glycol 1000 succinate, sucrose monostearate, sucrose distearate, sucrose monolaurate, sucrose dilaurate, sorbitan mono laurate, sorbitan monooleate, sorbitan monopalmitate, or sorbitan stearate, or a combination thereof. Other suitable ionic or non-ionic surfactants may also be used.

In yet another embodiment of this aspect of the invention, the solid dispersion is an amorphous solid dispersion. In still another embodiment, the solid dispersion is an amorphous solid dispersion which comprises (1) a compound selected from Compound $I_A$, $I_B$ or $I_C$, or a pharmaceutically acceptable salt thereof, (2) the hydrophilic polymer, and (3) the surfactant. In a further embodiment, the solid dispersion is a solid solution comprising (1) a compound selected from Compound $I_A$, $I_B$ or $I_C$, or a pharmaceutically acceptable salt thereof, and (2) the hydrophilic polymer. In yet another embodiment, the solid dispersion is a solid solution comprising (1) a compound selected from Compound $I_A$, $I_B$ or $I_C$, or a pharmaceutically acceptable salt thereof, (2) the hydrophilic polymer, and (3) the surfactant.

In yet another embodiment of this aspect of the invention, the hydrophilic polymer is a homopolymer or copolymer of N-vinyl pyrrolidone. Preferably, the hydrophilic polymer is copovidone.

In still another embodiment, the surfactant is D-alpha-tocopheryl polyethylene glycol 1000 succinate (vitamin E TPGS). In a further embodiment, the surfactant is lauroglycol FCC. In yet another embodiment, the surfactant is a combination of vitamin E TPGS and lauroglycol FCC. In still another embodiment, the surfactant is a sorbitan fatty acid ester, such as sorbitan mono laurate (Span 20). In another embodiment, the surfactant is selected from Tween 20, Tween 80, vitamin E TPGS, or lauroglycol FCC, or a combination thereof.

In yet another embodiment, a solid composition of the invention comprises an amorphous solid dispersion or a solid solution which comprises (1) a compound selected from Compound $I_A$, $I_B$ or $I_C$, or a pharmaceutically acceptable salt thereof, (2) copovidone, and (3) a surfactant selected from vitamin E TPGS, Span 20, or a combination thereof.

In another embodiment, a solid composition of the invention comprises an amorphous solid dispersion or a solid solution which comprises (1) a compound selected from Compound $I_A$, $I_B$ or $I_C$, or a pharmaceutically acceptable salt thereof, (2) copovidone, and (3) a combination of vitamin E TPGS and lauroglycol FCC.

In still another embodiment, a solid composition of the invention comprises an amorphous solid dispersion or a solid solution which comprises (1) a compound selected from Compound $I_A$, $I_B$ or $I_C$, or a pharmaceutically acceptable salt thereof, (2) copovidone, and (3) a surfactant selected from Tween 20 or Tween 80.

In another aspect, the present invention features processes of making a solid composition of the present invention. In one embodiment, the process comprises drying a solvent in a liquid solution, wherein said solution comprises: (1) a compound selected from Compound $I_A$, $I_B$ or $I_C$, or a pharmaceutically acceptable salt thereof; (2) a pharmaceutically acceptable hydrophilic polymer; and optionally (3) a pharmaceutically acceptable surfactant. The drying process can be carried out using any suitable solvent evaporation techniques including but not limited to spray-drying techniques.

In another embodiment, the process comprises solidifying a melt which comprises: (1) a compound selected from Compound $I_A$, $I_B$ or $I_C$, or a pharmaceutically acceptable salt thereof; (2) a pharmaceutically acceptable hydrophilic polymer; and optionally (3) a pharmaceutically acceptable surfactant.

A solid composition of the invention may also contain other additives or ingredients, such as coloring agents, flavoring agents, lubricants or preservatives. A solid composition of the invention can be prepared into any suitable dosage forms, such as capsule, dragee, granule, powder, or tablet.

A solid composition of the invention may further comprise another anti-HCV agent, for example, an agent selected from HCV helicase inhibitors, HCV polymerase inhibitors, HCV protease inhibitors, HCV NS5A inhibitors, CD81 inhibitors, cyclophilin inhibitors, or internal ribosome entry site (IRES) inhibitors.

The present invention further features methods of using a solid composition of the present invention to treat HCV infection. The methods comprise administering a solid composition of the present invention to a patient in need thereof, thereby reducing the blood or tissue level of HCV virus in the patient.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features solid compositions comprising (1) a compound selected from Compound $I_A$, $I_B$ or $I_C$, or a pharmaceutically acceptable salt thereof, in an amorphous form, (2) a pharmaceutically acceptable hydrophilic polymer, and optionally (3) a pharmaceutically acceptable surfactant. Formulating Compound $I_A$, $I_B$ and $I_C$ in an amorphous form can increase the inherent drug solubility and dissolution rate, thereby enhancing the bioavailability of the compound.

A non-limiting way to form an amorphous form of Compound $I_A$, $I_B$ or $I_C$ (or a pharmaceutically acceptable salt thereof) is through the formation of solid dispersions with a polymeric carrier. The presence of hydrophilic polymer(s) and optional surfactant(s), as well as the dispersion of Compound $I_A$, $I_B$ or $I_C$ (or a pharmaceutically acceptable salt thereof) in an amorphous form in a matrix containing the polymer(s), can significantly enhance the dissolution rate of the compound. In some cases, a solid dispersion formulation can also effectively maintain Compound $I_A$, $I_B$ or $I_C$ (or a pharmaceutically acceptable salt thereof) in its supersaturation state to allow for better absorption.

As used herein, the term "solid dispersion" defines a system in a solid state (as opposed to a liquid or gaseous state) comprising at least two components, wherein one component is dispersed throughout the other component or components. For example, an active ingredient or a combination of active ingredients can be dispersed in a matrix comprised of a pharmaceutically acceptable hydrophilic polymer(s) and a pharmaceutically acceptable surfactant(s). The term "solid dispersion" encompasses systems having small particles of one phase dispersed in another phase. These particles are often of less than 400 µm in size, such as less than 100, 10, or 1 µm in size. When a solid dispersion of the components is such that the system is chemically and physically uniform or homogenous throughout or consists of one phase (as defined in thermodynamics), such a solid dispersion is called a "solid solution." A glassy solution is a solid solution in which a solute is dissolved in a glassy solvent.

The term $AUC_\infty$ or $AUC_{0\text{-}inf}$ refers to the area under the plasma concentration time curve (AUC) extrapolated to infinity.

The terms "weight percent" or "percent by weight" or "% by weight" or "wt %" denote the weight of an individual component in a composition or mixture as a percentage of the weight of the composition or mixture.

In one aspect, the present invention features a solid composition comprising (1) a compound selected from Compound $I_A$, $I_B$ or $I_C$, or a pharmaceutically acceptable salt thereof, in an amorphous form, (2) a pharmaceutically acceptable hydrophilic polymer, and (3) a pharmaceutically acceptable surfactant. The compound (or the salt thereof) and the polymer are formulated in a solid dispersion. The surfactant may be formulated in the same solid dispersion; or the surfactant can be separately combined or mixed with the solid dispersion.

In one embodiment, a solid composition of the invention comprises an amorphous solid dispersion which comprises (1) a compound selected from Compound $I_A$, $I_B$ or $I_C$, or a pharmaceutically acceptable salt thereof, (2) a pharmaceutically acceptable hydrophilic polymer, and (3) a pharmaceutically acceptable surfactant. In another embodiment, a solid composition of the invention comprises a solid solution which comprises (1) a compound selected from Compound $I_A$, $I_B$ or $I_C$, or a pharmaceutically acceptable salt thereof, and (2) a pharmaceutically acceptable hydrophilic polymer. In still another embodiment, a solid composition of the invention comprises a solid solution which comprises (1) a compound selected from Compound $I_A$, $I_B$ or $I_C$, or a pharmaceutically acceptable salt thereof, (2) a pharmaceutically acceptable hydrophilic polymer, and (3) a pharmaceutically acceptable surfactant. In yet another embodiment, a solid composition of the invention comprises a glassy solution which includes (1) a compound selected from Compound $I_A$, $I_B$ or $I_C$, or a pharmaceutically acceptable salt thereof, and (2) a pharmaceutically acceptable hydrophilic polymer. In a further embodiment, a solid composition of the invention comprises a glassy solution which includes (1) a compound selected from Compound $I_A$, $I_B$ or $I_C$, or a pharmaceutically acceptable salt thereof, (2) a pharmaceutically acceptable hydrophilic polymer, and (3) a pharmaceutically acceptable surfactant.

A solid composition (or a solid dispersion) of the invention can contain, for example, at least 1% by weight of Compound $I_A$, $I_B$ or $I_C$ (or a pharmaceutically acceptable salt thereof), preferably at least 5%, including, e.g., at least 10%. For instance, a solid composition (or a solid dispersion) of the invention can contain from 1 to 50% by weight of the compound (or the salt thereof). For another instance, a solid composition (or a solid dispersion) of the invention can contain from 5 to 30% by weight of the compound (or the salt thereof). Preferably, a solid composition (or a solid dispersion) of the invention contains from 5 to 15% by weight of the compound (or the salt thereof).

A solid dispersion of the invention may contain at least 30% by weight of a pharmaceutically acceptable hydrophilic polymer or a combination of such hydrophilic polymers. Preferably, the solid dispersion contains at least 40% by weight of a pharmaceutically acceptable hydrophilic polymer or a combination of such hydrophilic polymers. More preferably, the solid dispersion contains at least 50% (including, e.g., at least 60%, 70%, 80% or 90%) by weight of a pharmaceutically acceptable hydrophilic polymer or a combination of such polymers. A solid dispersion (or a solid composition) of the invention may also contain at least 1% by weight of a pharmaceutically acceptable surfactant or a combination of such surfactants. Preferably, the solid dispersion (or solid composition) contains at least 2% by weight of a pharmaceutically acceptable surfactant or a combination of such surfactants. More preferably, the solid dispersion (or solid composition) contains from 4% to 20% by weight of the surfactant(s), such as from 5% to 10% by weight of the surfactant(s).

In one embodiment, a solid dispersion (or a solid composition) of the invention comprises at least 30% by weight of a pharmaceutically acceptable hydrophilic polymer or a combination of such polymers, and at least 1% by weight of a pharmaceutically acceptable surfactant or a combination of such surfactants. In another embodiment, a solid dispersion (or a solid composition) of the invention comprises at least 50% by weight of a pharmaceutically acceptable hydrophilic polymer or a combination of such polymers, and from 2% to 20% by weight of a pharmaceutically acceptable surfactant or a combination of such surfactants. In yet another embodiment, a solid dispersion (or a solid composition) of the invention comprises from 50% to 90% by weight of a pharmaceutically acceptable hydrophilic polymer or a combination of such polymers, and from 3% to 15% by weight of a pharmaceutically acceptable surfactant or a combination of such surfactants. In yet another embodiment, a solid dispersion (or a solid composition) of the invention comprises from 70% to 90% by weight of a pharmaceutically acceptable hydrophilic polymer or a combination of such polymers, and from 5% to 10% by weight of a pharmaceutically acceptable surfactant or a combination of such surfactants.

Preferably, a hydrophilic polymer employed in the present invention has a $T_g$ of at least 50° C., more preferably at least 60° C., and highly preferably at least 80° C. including, but not limited to from, 80° C. to 180° C., or from 100° C. to 150° C. Methods for determining $T_g$ values of organic polymers are described in INTRODUCTION TO PHYSICAL POLYMER SCIENCE (2nd Edition by L. H. Sperling, published by John Wiley & Sons, Inc., 1992). The $T_g$ value can be calculated as the weighted sum of the $T_g$ values for homopolymers derived from each of the individual monomers, i.e., the polymer $T_g = \Sigma W_i \cdot X_i$ where $W_i$ is the weight percent of monomer i in the organic polymer, and $X_i$ is the $T_g$ value for the homopolymer derived from monomer i. $T_g$ values for the homopolymers may be taken from POLYMER HANDBOOK (2nd Edition by J. Brandrup and E. H. Immergut, Editors, published by John Wiley & Sons, Inc., 1975). Hydrophilic polymers with a $T_g$ as described above may allow for the preparation of solid dispersions that are mechanically stable and, within ordinary temperature ranges, sufficiently temperature stable so that the solid dispersions may be used as dosage forms without further processing or be compacted to tablets with only a small amount of tabletting aids. Hydrophilic polymers having a $T_g$ of below 50° C. may also be used.

Preferably, a hydrophilic polymer employed in the present invention is water-soluble. A solid composition of the present invention can also comprise poorly water-soluble or water-insoluble polymer or polymers, such as cross-linked polymers. A hydrophilic polymer comprised in a solid composition of the present invention preferably has an apparent viscosity, when dissolved at 20° C. in an aqueous solution at 2% (w/v), of 1 to 5000 mPa·s, and more preferably of 1 to 700 mPa·s, and most preferably of 5 to 100 mPa·s.

Hydrophilic polymers suitable for use in a solid composition of the invention include, but are not limited to, homopolymers or copolymers of N-vinyl lactams, such as homopolymers or copolymers of N-vinyl pyrrolidone (e.g., polyvinylpyrrolidone (PVP), or copolymers of N-vinyl pyrrolidone and vinyl acetate or vinyl propionate); cellulose esters or cellulose ethers, such as alkylcelluloses (e.g., methylcellulose or ethylcellulose), hydroxyalkylcelluloses (e.g., hydroxypropylcellulose), hydroxyalkylalkylcelluloses (e.g., hydroxypropylmethylcellulose), and cellulose phthalates or succinates (e.g., cellulose acetate phthalate and hydroxypropylmethylcellulose phthalate, hydroxypropylmethylcellulose succinate, or hydroxypropylmethylcellulose acetate succinate); high molecular polyalkylene oxides, such as polyethylene oxide, polypropylene oxide, and copolymers of ethylene oxide and propylene oxide; polyacrylates or polymethacrylates, such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), and poly(hydroxyalkyl methacrylates); polyacrylamides; vinyl acetate polymers, such as copolymers of vinyl acetate and crotonic acid, and partially hydrolyzed polyvinyl acetate (also referred to as partially saponified "polyvinyl alcohol"); polyvinyl alcohol; oligo- or polysaccharides, such as carrageenans, galactomannans, and xanthan gum; polyhydroxyalkylacrylates; polyhydroxyalkyl-methacrylates; copolymers of methyl methacrylate and acrylic acid; polyethylene glycols (PEGs); graft copolymers of polyethylene glycol/polyvinyl caprolactam/polyvinyl acetate, or any mixture or combination thereof. In some cases, sugar alcohols can be used in addition to, or in lieu of, hydrophilic polymers.

Non-limiting examples of preferred hydrophilic polymers for the invention include polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, Soluplus, poloxamer 124, poloxamer 188, poloxamer 237, poloxamer 338, and poloxamer 407.

Of these, homopolymers or copolymers of N-vinyl pyrrolidone, such as copolymers of N-vinyl pyrrolidone and vinyl acetate, are preferred. A non-limiting example of a preferred polymer is a copolymer of 60% by weight of N-vinyl pyrrolidone and 40% by weight of vinyl acetate. Other preferred polymers include, without limitation, hydroxypropyl methylcellulose (HPMC, also known as hypromellose in USP), such as hydroxypropyl methylcellulose grade E5 (HPMC-E5); and hydroxypropyl methylcellulose acetate succinate (HPMC-AS).

A pharmaceutically acceptable surfactant employed in the present invention is preferably a non-ionic surfactant. Ionic surfactants may also be used. More preferably, a solid composition of the present invention comprises a pharmaceutically acceptable surfactant having an HLB value of from 2-20. A solid composition of the present invention can also include a mixture of pharmaceutically acceptable surfactants, with at least one surfactant having an HLB value of no less than 10 and at least another surfactant having an HLB value of below 10. In one example, each surfactant comprised in a solid composition of the invention has an HLB value of at least 10. In another example, each surfactant comprised in a solid composition of the invention has an HLB value of below 10. In yet another example, a solid composition of the present invention includes at least two pharmaceutically acceptable surfactants, one having an HLB value of at least 10 and the other having an HLB value of below 10. The HLB system (Fiedler, H. B., ENCYCLOPEDIA OF EXCIPIENTS, 5$^{th}$ ed., Aulendorf: ECV-Editio-Cantor-Verlag (2002)) attributes numeric values to surfactants, with lipophilic substances receiving lower HLB values and hydrophilic substances receiving higher HLB values.

Non-limiting examples of pharmaceutically acceptable surfactants that are suitable for the present invention include polyoxyethylene castor oil derivates, e.g. polyoxyethyleneglycerol triricinoleate or polyoxyl 35 castor oil (Cremophor EL; BASF Corp.) or polyoxyethyleneglycerol oxystearate such as polyethylenglycol 40 hydrogenated castor oil (Cremophor RH 40, also known as polyoxyl 40 hydrogenated castor oil or macrogolglycerol hydroxystearate) or polyethylenglycol 60 hydrogenated castor oil (Cremophor RH 60); or a mono fatty acid ester of polyoxyethylene sorbitan, such as a mono fatty acid ester of polyoxyethylene (20) sorbitan, e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20). Other non-limiting examples of suitable surfactants include polyoxyethylene alkyl ethers, e.g. polyoxyethylene (3) lauryl ether, polyoxyethylene (5) cetyl ether, polyoxyethylene (2) stearyl ether, polyoxyethylene (5) stearyl ether; polyoxyethylene alkylaryl ethers, e.g. polyoxyethylene (2) nonylphenyl ether, polyoxyethylene (3) nonylphenyl ether, polyoxyethylene (4) nonylphenyl ether, polyoxyethylene (3) octylphenyl ether; polyethylene glycol fatty acid esters, e.g. PEG-200 monolaurate, PEG-200 dilaurate, PEG-300 dilaurate, PEG-400 dilaurate, PEG-300 distearate, PEG-300 dioleate; alkylene glycol fatty acid mono esters, e.g. propylene glycol monolaurate (lauroglycol, such as lauroglycol FCC); sucrose fatty acid esters, e.g. sucrose monostearate, sucrose distearate, sucrose monolaurate, sucrose dilaurate; sorbitan fatty acid mono esters such as sorbitan mono laurate (Span 20), sorbitan monooleate, sorbitan monopalnitate (Span 40), or sorbitan stearate; D-alpha-tocopheryl polyethylene glycol 1000 succinate; or a combination or mixture thereof. Other suitable surfactants include, but are not limited to, block copolymers of ethylene oxide and propylene oxide, also known as polyoxyethylene polyoxypropylene block copolymers or polyoxyethylene polypropyleneglycol, such as Poloxamer 124, Poloxamer 188, Poloxamer 237, Poloxamer 388, or Poloxamer 407 (BASF Wyandotte Corp.). As described above, a mixture of surfactants can be used in a solid composition of the present invention.

Non-limiting examples of preferred surfactants for the invention include to polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, and sorbitan monolaurate.

In one embodiment, a solid composition of the present invention comprises an amorphous solid dispersion or solid solution which includes (1) a compound selected from Compound $I_A$, $I_B$ or $I_C$, or a pharmaceutically acceptable salt thereof, and (2) a pharmaceutically acceptable hydrophilic polymer. The solid composition also includes a pharmaceutically acceptable surfactant which preferably is formulated in the amorphous solid dispersion or solid solution. The hydrophilic polymer can be selected, for example, from the group consisting of homopolymer of N-vinyl lactam, copolymer of N-vinyl lactam, cellulose ester, cellulose ether, polyalkylene oxide, polyacrylate, polymethacrylate, polyacrylamide, polyvinyl alcohol, vinyl acetate polymer, oligosaccharide, and polysaccharide. As a non-limiting example, the hydrophilic polymer is selected from the group consisting of homopolymer of N-vinyl pyrrolidone, copolymer of N-vinyl pyrrolidone, copolymer of N-vinyl pyrrolidone and vinyl acetate, copolymer of N-vinyl pyrrolidone and vinyl propionate, polyvinylpyrrolidone, methylcellulose, ethylcellulose, hydroxyalkylcelluloses, hydroxypropylcellulose, hydroxyalkylalkylcellulose, hydroxypropylmethylcellulose, cellulose phthalate, cellulose succinate, cellulose acetate phthalate, hydroxypropylmethylcellulose phthalate, hydroxypropylmethylcellulose succinate, hydroxypropylmethylcellulose acetate succinate, polyethylene oxide, polypropylene oxide, copolymer of ethylene oxide and propylene oxide, graft copolymer of polyethylene glycol/polyvinyl caprolactam/polyvinyl acetate, methacrylic acid/ethyl acrylate copolymer, methacrylic acid/methyl methacrylate copolymer, butyl methacrylate/2-dimethylaminoethyl methacrylate copolymer, poly(hydroxyalkyl acrylate), poly(hydroxyalkyl methacrylate), copolymer of vinyl acetate and crotonic acid, partially hydrolyzed polyvinyl acetate, carrageenan, galactomannan, and xanthan gum. Preferably, the hydrophilic polymer is selected from polyvinylpyrrolidone (PVP) K17, PVP K25, PVP K30, PVP K90, hydroxypropyl methylcellulose (HPMC) E3, HPMC E5, HPMC E6, HPMC E15, HPMC K3, HPMC A4, HPMC A15, HPMC acetate succinate (AS) LF, HPMC AS MF, HPMC AS HF, HPMC AS LG, HPMC AS MG, HPMC AS HG, HPMC phthalate (P) 50, HPMC P 55, Ethocel 4, Ethocel 7, Ethocel 10, Ethocel 14, Ethocel 20, copovidone (vinylpyrrolidone-vinyl acetate copolymer 60/40), polyvinyl acetate, methacrylate/methacrylic acid copolymer (Eudragit) L100-55, Eudragit L100, Eudragit S100, polyethylene glycol (PEG) 400, PEG 600, PEG 1450, PEG 3350, PEG 4000, PEG 6000, PEG 8000, Soluplus, poloxamer 124, poloxamer 188, poloxamer 237, poloxamer 338, or poloxamer 407. More preferably, the hydrophilic polymer is selected from homopolymers of vinylpyrrolidone (e.g., PVP with Fikentscher K values of from 12 to 100, or PVP with Fikentscher K values of from 17 to 30), or copolymers of 30 to 70% by weight of N-vinylpyrrolidone (VP) and 70 to 30% by weight of vinyl acetate (VA) (e.g., a copolymer of 60% by weight VP and 40% by weight VA). The surfactant can be selected, for example, from the group consisting of polyoxyethyleneglycerol triricinoleate or polyoxyl 35 castor oil (Cremophor EL; BASF Corp.) or polyoxyethyleneglycerol oxystearate, mono fatty acid ester of polyoxyethylene sorbitan, polyoxyethylene alkyl ether, polyoxyethylene alkylaryl ether, polyethylene glycol fatty acid ester, alkylene glycol fatty acid mono ester, sucrose fatty acid ester, and sorbitan fatty acid mono ester. As a non-limited example, the surfactant is selected from the group consisting of polyethylenglycol 40 hydrogenated castor oil (Cremophor RH 40, also known as polyoxyl 40 hydrogenated castor oil or macrogolglycerol hydroxystearate), polyethylenglycol 60 hydrogenated castor oil (Cremophor RH 60), a mono fatty acid ester of polyoxyethylene (20) sorbitan (e.g. polyoxyethylene (20) sorbitan monooleate (Tween 80), polyoxyethylene (20) sorbitan monostearate (Tween 60), polyoxyethylene (20) sorbitan monopalmitate (Tween 40), or polyoxyethylene (20) sorbitan monolaurate (Tween 20)), polyoxyethylene (3) lauryl ether, polyoxyethylene (5) cetyl ether, polyoxyethylene (2) stearyl ether, polyoxyethylene (5) stearyl ether, polyoxyethylene (2) nonylphenyl ether, polyoxyethylene (3) nonylphenyl ether, polyoxyethylene (4) nonylphenyl ether, polyoxyethylene (3) octylphenyl ether, PEG-200 monolaurate, PEG-200 dilaurate, PEG-300 dilaurate, PEG-400 dilaurate, PEG-300 distearate, PEG-300 dioleate, propylene glycol monolaurate, D-alpha-tocopheryl polyethylene glycol 1000 succinate, sucrose monostearate, sucrose distearate, sucrose monolaurate, sucrose dilaurate, sorbitan monolaurate, sorbitan monooleate, sorbitan monopalnitate, and sorbitan stearate. Preferably, the surfactant is selected from polysorbate 20, polysorbate 40, polysorbate 60, polysorbate 80, Cremophor RH 40, Cremophor EL, Gelucire 44/14, Gelucire 50/13, D-alpha-tocopheryl polyethylene glycol 1000 succinate (vitamin E TPGS), propylene glycol laurate, sodium lauryl sulfate, or sorbitan monolaurate. More preferably, the surfactant is selected from sorbitan monolaurate, D-alpha-tocopheryl polyethylene glycol 1000 succinate, propylene glycol monolaurate, or a combination thereof (e.g., a combination of D-alpha-tocopheryl polyethylene glycol 1000 succinate and lauroglycol FCC).

In another embodiment, a solid composition of the present invention comprises an amorphous solid dispersion or solid solution which includes (1) a compound selected from Compound $I_A$, $I_B$ or $I_C$, or a pharmaceutically acceptable salt thereof, and (2) a homopolymer or copolymer of N-vinyl pyrrolidone (e.g., copovidone). The solid composition also comprises a pharmaceutically acceptable surfactant (e.g., vitamin E TPGS, sorbitan monolaurate, or a combination of vitamin E TPGS and lauroglycol FCC), wherein the surfactant preferably is formulated in the amorphous solid dispersion or solid solution.

In yet another embodiment, a solid composition of the present invention comprises an amorphous solid dispersion or solid solution which includes (1) a compound selected from Compound $I_A$, $I_B$ or $I_C$, or a pharmaceutically acceptable salt thereof, (2) copovidone, and (3) a pharmaceutically acceptable surfactant (e.g., vitamin E TPGS, sorbitan monolaurate, or a combination of vitamin E TPGS and lauroglycol FCC). The amorphous solid dispersion or solid solution may also include another pharmaceutically acceptable surfactant.

In still another embodiment, a solid composition of the present invention comprises an amorphous solid dispersion or solid solution which includes (1) 10% by weight Compound $I_A$, $I_B$ or $I_C$ (or a pharmaceutically acceptable salt thereof) (2) 82% by weight copovidone, and (3) 5% by weight vitamin E TPGS and 2% by weight lauroglycol FCC. The solid composition can also include 1% by weight colloidal silica.

In a further embodiment, a solid composition of the present invention comprises an amorphous solid dispersion or solid solution which includes (1) 10% by weight Compound $I_A$, $I_B$ or $I_C$ (or a pharmaceutically acceptable salt thereof) (2) 82% by weight copovidone, and (3) 7% by weight propylene glycol monocaprylate (Capryol 90). The solid composition can also include 1% by weight colloidal silica.

A solid dispersion employed in the present invention preferably comprises or consists of a single-phase (defined in thermodynamics) in which the therapeutic agent(s) (e.g., Compound $I_A$, $I_B$ or $I_C$, or a pharmaceutically acceptable salt thereof, with or without another anti-HCV agent) is molecularly dispersed in a matrix containing the pharmaceutically acceptable hydrophilic polymer(s). In such cases, thermal analysis of the solid dispersion using differential scanning calorimetry (DSC) typically shows only one single $T_g$, and the solid dispersion does not contain any detectable crystalline Compound $I_A$, $I_B$ or $I_C$ as measured by X-ray powder diffraction spectroscopy.

Compound $I_A$, $I_B$ and $I_C$ can be prepared according to the procedures described in Examples 144, 250 and 237, respectively, of U.S. patent application Ser. No. 12/813,301, filed Jun. 10, 2010, now U.S. Patent Application Publication No. 2010/0317568, which is incorporated herein by reference in its entirety.

A solid composition of the present invention can further include one or more other anti-HCV agents. These other anti-HCV agents can be, for example, HCV polymerase inhibitors (including nucleoside or non-nucleoside type of polymerase inhibitors), HCV protease inhibitors, HCV helicase inhibitors, CD81 inhibitors, cyclophilin inhibitors, internal ribosome entry site inhibitors, or HCV NS5A inhibitors. Specific examples of these other anti-HCV agents include, but are not limited to, ribavirin, α-interferon, β-interferon, pegylated interferon-α, pegylated interferon-lambda, PSI-7851 (Pharmasset) (nucleoside polymerase inhibitor), PSI-938 (Pharmasset) (nucleoside polymerase inhibitor), PF-00868554, ANA-598, IDX184 (nucleoside polymerase inhibitor), IDX102, IDX375 (non-nucleoside polymerase inhibitor), GS-9190 (non-nucleoside polymerase inhibitor), VCH-759, VCH-916, MK-3281, BCX-4678, MK-3281, VBY708, ANA598, GL59728, GL60667, BMS-790052 (NS5A inhibitor), BMS-791325 (protease Inhibitor), BMS-650032, BMS-824393, GS-9132, ACH-1095 (protease inhibitor), AP-H005, A-831 (Arrow Therapeutics) (NS5A inhibitor), A-689 (Arrow Therapeutics) (NS5A inhibitor), INX08189 (Inhibitex) (polymerase inhibitor), AZD2836, telaprevir (protease Inhibitor), boceprevir (protease Inhibitor), ITMN-191 (Intermune/Roche), BI-201335 (protease Inhibitor), VBY-376, VX-500 (Vertex) (protease Inhibitor), PHX-B, ACH-1625, IDX136, IDX316, VX-813 (Vertex) (protease Inhibitor), SCH 900518 (Schering-Plough), TMC-435 (Tibotec) (protease Inhibitor), ITMN-191 (Intermune, Roche) (protease Inhibitor), MK-7009 (Merck) (protease Inhibitor), IDX-PI (Novartis), BI-201335 (Boehringer Ingelheim), R7128 (Roche) (nucleoside polymerase inhibitor), MK-3281 (Merck), MK-0608 (Merck) (nucleoside polymerase inhibitor), PF-868554 (Pfizer) (non-nucleoside polymerase inhibitor), PF-4878691 (Pfizer), IDX-184 (Novartis), IDX-375 (Pharmasset), PPI-461 (Presidio) (NS5A inhibitor), BILB-1941 (Boehringer Ingelheim), GS-9190 (Gilead), BMS-790052 (BMS), Albuferon (Novartis), ABT-333 (Abbott) (non-nucleoside polymerase inhibitor), and ABT-072 (Abbott) (non-nucleoside polymerase inhibitor).

In one embodiment, a solid composition of the invention comprises Compound $I_A$, $I_B$ or $I_C$ (or a pharmaceutically acceptable salt thereof), and a HCV protease inhibitor. In another embodiment, a solid composition of the invention comprises Compound $I_A$, $I_B$ or $I_C$ (a pharmaceutically acceptable salt thereof), and a HCV polymerase inhibitor (e.g., a non-nucleoside polymerase inhibitor, or preferably a nucleoside polymerase inhibitor). In yet another embodiment, a solid composition of the invention comprises (1) Compound $I_A$, $I_B$ or $I_C$ (a pharmaceutically acceptable salt thereof), (2) a HCV protease inhibitor, and (3) a HCV polymerase inhibitor (e.g., a non-nucleoside polymerase inhibitor, or preferably a nucleoside polymerase inhibitor). Non-limiting examples of protease and polymerase inhibitors are described above. For instance, the protease inhibitor can be selected from ACH-1095 (Achillion), ACH-1625 (Achillion), ACH-2684 (Achillion), AVL-181 (Avila), AVL-192 (Avila), BI-201335 (Boehringer Ingelheim), BMS-650032 (BMS), boceprevir, danoprevir, GS-9132 (Gilead), GS-9256 (Gilead), GS-9451 (Gilead), IDX-136 (Idenix), IDX-316 (Idenix), IDX-320 (Idenix), MK-5172 (Merck), narlaprevir, PHX-1766 (Phenomix), telaprevir, TMC-435 (Tibotec), vaniprevir, VBY708 (Virobay), VX-500 (Vertex), VX-813 (Vertex), VX-985 (Vertex), or a combination thereof. And the HCV polymerase inhibitor can be selected from, without limitation, ABT-072 (Abbott), ABT-333 (Abbott), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-222 (VCH-222) (Vertex & ViraChem), VX-759 (Vertex), GS-6620 (Gilead), IDX-102 (Idenix), IDX-184 (Idenix), INX-189 (Inhibitex), MK-0608 (Merck), PSI-7977 (Pharmasset), PSI-938 (Pharmasset), RG7128 (Roche), TMC64912 (Medivir), GSK625433 (GlaxoSmithKline), BCX-4678 (BioCryst), or a combination thereof. The polymerase inhibitor may be a nucleotide polymerase inhibitor, such as GS-6620 (Gilead), IDX-102 (Idenix), IDX-184 (Idenix), INX-189 (Inhibitex), MK-0608 (Merck), PSI-7977 (Pharmasset), PSI-938 (Pharmasset), RG7128 (Roche), TMC64912 (Medivir), or a combination therefore. The polymerase inhibitor may also be a non-nucleoside polymerase inhibitor, such as ABT-072 (Abbott), ABT-333 (Abbott), ANA-598 (Anadys), BI-207127 (Boehringer Ingelheim), BILB-1941 (Boehringer Ingelheim), BMS-791325 (BMS), filibuvir, GL59728 (Glaxo), GL60667 (Glaxo), GS-9669 (Gilead), IDX-375 (Idenix), MK-3281 (Merck), tegobuvir, TMC-647055 (Tibotec), VCH-759 (Vertex & ViraChem), VCH-916 (ViraChem), VX-222 (VCH-222) (Vertex & ViraChem), VX-759 (Vertex), or a combination thereof. The present invention also contemplates the inclusion of both a nucleotide polymerase inhibitor and a non-nucleoside polymerase inhibitor in a solid composition of the invention.

In yet another embodiment, a solid composition of the invention comprises (1) Compound $I_A$, $I_B$, or $I_C$ (a pharmaceutically acceptable salt thereof), and (2) INX-189

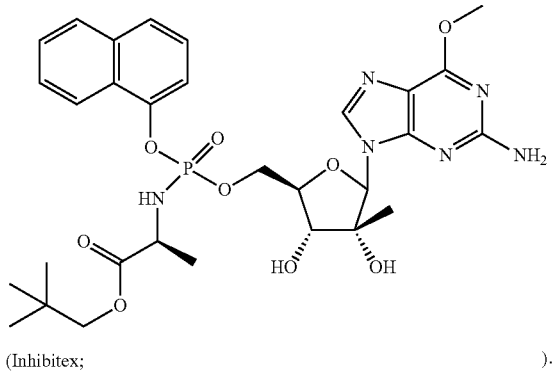 [SMILES: COc1nc(N)nc2c1ncn2C1O[C@H](COP(=O)(N[C@@H](C)C(=O)OCC(C)(C)C)Oc2cccc3ccccc23)[C@@H](O)[C@@]1(C)O]

(Inhibitex; ).

In still another embodiment, a solid composition of the invention comprises (1) Compound $I_A$, $I_B$, or $I_C$ (a pharmaceutically acceptable salt thereof), and (2) RG7128, PSI-7977, PSI-938 or PSI-7851. In a further embodiment, a solid composition of the invention comprises (1) Compound $I_A$, $I_B$, or $I_C$ (a pharmaceutically acceptable salt thereof), (2) MK-5172, and optionally (3) RG7128. In another embodiment, a solid composition of the invention comprises (1) Compound $I_A$, $I_B$, or $I_C$ (a pharmaceutically acceptable salt thereof), (2) BMS-650032, and optionally (3) PSI-7977, PSI-938 or PSI-7851. In another embodiment, a solid composition of the invention comprises (1) Compound $I_A$, $I_B$, or $I_C$ (a pharmaceutically acceptable salt thereof), (2) danoprevir, and optionally (3) RG7128, PSI-7977, PSI-938 or PSI-7851. In another embodiment, a solid composition of the invention comprises (1) Compound $I_A$, $I_B$, or $I_C$ (a pharmaceutically acceptable salt thereof), (2) TMC-435, and optionally (3) RG7128, PSI-7977, PSI-938 or PSI-7851. In another embodiment, a solid composition of the invention comprises (1) Compound $I_A$, $I_B$, or $I_C$ (a pharmaceutically acceptable salt thereof), (2) BMS-650032, and optionally (3) BMS-790052. Compound $I_A$, $I_B$, or $I_C$ (a pharmaceutically acceptable salt thereof), and BMS-790052, can be co-formulated in an amorphous form, e.g., co-formulated in a solid dispersion or solid solution described herein. In still another embodiment, a solid composition of the invention comprises (1) Compound $I_A$, $I_B$, or $I_C$ (a pharmaceutically acceptable salt thereof), and (2) GS-9256, GS-9190, GS-9132, GS-9451, GS-9669, or GS-6620.

Compound $I_A$, $I_B$, or $I_C$ (a pharmaceutically acceptable salt thereof), and one or more other anti-HCV agents described herein (e.g., MX-5172 or danoprevir), can be co-formulated in amorphous forms, e.g., co-formulated in a solid dispersion or solid solution described herein. Alternatively, Compound $I_A$, $I_B$, or $I_C$ (a pharmaceutically acceptable salt thereof) can be co-administered with one or more other anti-HCV agents described herein, either concurrently or sequentially, to a patient in need thereof for the treatment of HCV infection.

A solid composition of the present invention preferably is a solid oral dosage form. Common solid oral dosage forms suitable for the present invention include, but are not limited to, capsules, dragees, granules, pills, powders and tablets, with capsules and tablets being preferred. A solid oral dosage form of the present invention can also include other excipients or inset diluents, such as sucrose, lactose or starch. Lubricants, coloring agents, releasing agents, coating agents, sweetening or flavoring agents, buffering agents, preservatives, or antioxidants can also be included in a solid oral dosage form of the present invention.

A solid composition of the present invention can be prepared by a variety of techniques such as, without limitation, melt-extrusion, spray-drying, co-precipitation, freeze drying, or other solvent evaporation techniques, with melt-extrusion and spray-drying being preferred. The melt-extrusion process typically comprises the steps of preparing a melt which includes the active ingredient(s), the hydrophilic polymer(s) and preferably the surfactant(s), and then cooling the melt until it solidifies. Melting often involves a transition into a liquid state in which it is possible for one component to get dissolved or embedded, preferably homogeneously dissolved or embedded, in the other component or components. In many cases, the polymer component(s) will melt and the other components including the active ingredient(s) and surfactant(s) will dissolve in the melt thereby forming a solution. In such a case, the polymer functions as a solvent. Melting usually involves heating above the softening point of the polymer(s). The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). In one example, all materials except surfactant(s) are blended and fed into an extruder, while the surfactant(s) is molten externally and pumped in during extrusion.

In another example, the melt comprises Compound $I_A$, $I_B$ or $I_C$ (a pharmaceutically acceptable salt thereof), and one or more hydrophilic polymers described above; and the melt temperature is in the range of from 100 to 170° C., preferably from 120 to 150° C., and highly preferably from 135 to 140° C. The melt can also include a pharmaceutically acceptable surfactant described above.

In still another example, the melt comprises Compound $I_A$, $I_B$ or $I_C$ (a pharmaceutically acceptable salt thereof), at least another anti-HCV agent described above, and one or more hydrophilic polymers described above. The melt can also include a pharmaceutically acceptable surfactant described above.

To start a melt-extrusion process, the active ingredient(s) (e.g., Compound $I_A$, $I_B$ or $I_C$ (a pharmaceutically acceptable salt thereof), or a combination of Compound $I_A$, $I_B$ or $I_C$ (a pharmaceutically acceptable salt thereof) with at least another anti-HCV agent) can be employed in their solid forms, such as their respective crystalline forms. The active ingredient(s) can also be employed as a solution or dispersion in a suitable liquid solvent such as alcohols, aliphatic hydrocarbons, esters or, in some cases, liquid carbon dioxide. The solvent can be removed, e.g. evaporated, upon preparation of the melt.

Various additives can also be included in the melt, for example, flow regulators (e.g., colloidal silica), binders, lubricants, fillers, disintegrants, plasticizers, colorants, or stabilizers (e.g., antioxidants, light stabilizers, radical scavengers, and stabilizers against microbial attack).

The melting and/or mixing can take place in an apparatus customary for this purpose. Particularly suitable ones are extruders or kneaders. Suitable extruders include single screw extruders, intermeshing screw extruders or multiscrew extruders, preferably twin screw extruders, which can be corotating or counterrotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The melt can range from thin to pasty to viscous. Shaping of the extrudate can be conveniently carried out by a calender with two counter-rotating rollers with mutually matching depressions on their surface. The extrudate can be cooled and allow to solidify. The extrudate can also be cut into pieces, either before (hot-cut) or after solidification (cold-cut).

The solidified extrusion product can be further milled, ground or otherwise reduced to granules. The solidified extrudate, as well as each granule produced, comprises a solid dispersion, preferably a solid solution, of the active ingredient(s) in a matrix comprised of the hydrophilic polymer(s) and optionally the pharmaceutically acceptable surfactant(s). Where the granules do not contain any surfactant, a pharmaceutically acceptable surfactant described above can be added to and blended with the granules. The extrusion product can also be blended with other active ingredient(s) and/or additive(s) before being milled or ground to granules. The granules can be further processed into suitable solid oral dosage forms.

In some cases, direct-shaping techniques such as injection moulding can be used in combination with melt extrusion to prepare suitable solid dosage forms.

In one example, copovidone and one or more surfactants are mixed and granulated, followed by the addition of aerosil and Compound $I_A$, $I_B$ or $I_C$ (a pharmaceutically acceptable salt thereof). The mixture, which may contain for example at least 5% by weight of Compound $I_A$, $I_B$ or $I_C$ (a pharmaceutically acceptable salt thereof) is then milled. The mixture is then subject to extrusion, and the extrudate thus produced can be milled and sieved for further processing to make capsules or tablets. Surfactant(s) employed in this example can also be added through liquid dosing during extrusion.

The approach of solvent evaporation, via spray-drying, provides the advantage of allowing for processability at lower temperatures, if needed, and allows for other modifications to the process in order to further improve powder properties. The spray-dried powder can then be formulated further, if needed, and final drug product is flexible with regards to whether capsule, tablet or any other solid dosage form is desired.

Exemplary spray-drying processes and spray-drying equipment are described in K. Masters, SPRAY DRYING HANDBOOK (Halstead Press, New York, $4^{th}$ ed., 1985). Non-limiting examples of spray-drying devices that are suitable for the present invention include spray dryers manufactured by Niro Inc. or GEA Process Engineering Inc., Buchi Labortechnik AG, and Spray Drying Systems, Inc. A spray-drying process generally involves breaking up a liquid mixture into small droplets and rapidly removing solvent from the droplets in a container (spray drying apparatus) where there is a strong driving force for evaporation of solvent from the droplets. Atomization techniques include, for example, two-fluid or pressure nozzles, or rotary atomizers. The strong driving force for solvent evaporation can be provided, for example, by maintaining the partial pressure of solvent in the spray drying apparatus well below the vapor pressure of the solvent at the temperatures of the drying droplets. This may be accomplished by either (1) maintaining the pressure in the spray drying apparatus at a partial vacuum; (2) mixing the liquid droplets with a warm drying gas (e.g., heated nitrogen); or (3) both.

The temperature and flow rate of the drying gas, as well as the spray dryer design, can be selected so that the droplets are dry enough by the time they reach the wall of the apparatus. This help to ensure that the dried droplets are essentially solid and can form a fine powder and do not stick to the apparatus wall. The spray-dried product can be collected by removing the material manually, pneumatically, mechanically or by other suitable means. The actual length of time to achieve the preferred level of dryness depends on the size of the droplets, the formulation, and spray dryer operation. Following the solidification, the solid powder may stay in the spray drying chamber for additional time (e.g., 5-60 seconds) to further evaporate solvent from the solid powder. The final solvent content in the solid dispersion as it exits the dryer is preferably at a sufficiently low level so as to improve the stability of the final product. For instance, the residual solvent content of the spray-dried powder can be less than 2% by weight. Highly preferably, the residual solvent content is within the limits set forth in the International Conference on Harmonization (ICH) Guidelines. In addition, it may be useful to subject the spray-dried composition to further drying to lower the residual solvent to even lower levels. Methods to further lower solvent levels include, but are not limited to, fluid bed drying, infra-red drying, tumble drying, vacuum drying, and combinations of these and other processes.

Like the solid extrudate described above, the spray dried product contains a solid dispersion, preferably a solid solution, of the active ingredient(s) in a matrix comprised of the hydrophilic polymer(s) and optionally the pharmaceutically acceptable surfactant(s). Where the spray dried product does not contain any surfactant, a pharmaceutically acceptable surfactant described above can be added to and blended with the spray-dried product before further processing.

Before feeding into a spray dryer, the active ingredient(s) (e.g., Compound $I_A$, $I_B$ or $I_C$ (a pharmaceutically acceptable salt thereof), or a combination of Compound $I_A$, $I_B$ or $I_C$ (a pharmaceutically acceptable salt thereof) with at least another anti-HCV agent), the hydrophilic polymer(s), as well as other optional active ingredients or excipients such as the pharmaceutically acceptable surfactant(s), can be dissolved in a solvent. Suitable solvents include, but are not limited to, water, alkanols (e.g., methanol, ethanol, 1-propanol, 2-propanol or mixtures thereof), acetone, acetone/water, alkanol/water mixtures (e.g., ethanol/water mixtures), or combinations thereof. The solution can also be preheated before being fed into the spray dryer.

The solid dispersion produced by melt-extrusion, spray-drying or other techniques can be prepared into any suitable solid oral dosage forms. In one embodiment, the solid dispersion prepared by melt-extrusion, spray-drying or other techniques (e.g., the extrudate or the spray-dried powder) can be compressed into tablets. The solid dispersion can be either directly compressed, or milled or ground to granules or powders before compression. Compression can be done in a tablet press, such as in a steel die between two moving punches. When a solid composition of the present invention comprises Compound $I_A$, $I_B$ or $I_C$ (a pharmaceutically acceptable salt thereof) and another anti-HCV agent, it is possible to separately prepare solid dispersions of each individual active ingredient and then blend the optionally milled or ground solid dispersions before compacting. Compound $I_A$, $I_B$ or $I_C$ (a pharmaceutically acceptable salt thereof) and other active ingredient(s) can also be prepared in the same solid dispersion, optionally milled and/or blended with other additives, and then compressed into tablets.

At least one additive selected from flow regulators, binders, lubricants, fillers, disintegrants, or plasticizers may be used in compressing the solid dispersion. These additives can be mixed with ground or milled solid dispersion before compacting. Disintegrants promote a rapid disintegration of the compact in the stomach and keeps the liberated granules separate from one another. Non-limiting examples of suitable disintegrants are cross-linked polymers such as cross-linked polyvinyl pyrrolidone, cross-linked sodium carboxymethylcellulose or sodium croscarmellose. Non-limiting examples of suitable fillers (also referred to as bulking agents) are lactose monohydrate, calcium hydrogenphosphate, microcrystalline cellulose (e.g., Avicell), silicates, in particular silicium dioxide, magnesium oxide, talc, potato or corn starch, isomalt, or polyvinyl alcohol. Non-limiting examples of suitable flow regulators include highly dispersed silica (e.g., colloidal silica such as Aerosil), and animal or vegetable fats or waxes. Non-limiting examples of suitable lubricants include polyethylene glycol (e.g., having a molecular weight of from 1000 to 6000), magnesium and calcium stearates, sodium stearyl fumarate, and the like.

Various other additives may also be used in preparing a solid composition of the present invention, for example dyes such as azo dyes, organic or inorganic pigments such as aluminium oxide or titanium dioxide, or dyes of natural origin; stabilizers such as antioxidants, light stabilizers, radical scavengers, stabilizers against microbial attack.

Solid compositions according to certain embodiments of the present invention may contain several layers, for example laminated or multilayer tablets. They can be in open or closed form. "Closed dosage forms" are those in which one layer is completely surrounded by at least one other layer.

In order to facilitate the intake of a solid dosage form, it is advantageous to give the dosage form an appropriate shape. Large tablets that can be swallowed comfortably are therefore preferably elongated rather than round in shape.

A film coat on the tablet further contributes to the ease with which it can be swallowed. A film coat also improves taste and provides an elegant appearance. The film-coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. polysorbates, and optionally a pigment, e.g. titanium dioxide or iron oxides. The film-coating may also comprise talc as anti-adhesive. Preferably, the film coat accounts for less than 5% by weight of a pharmaceutical composition of the present invention.

In another aspect, the present invention feature methods of using solid compositions of the present invention to treat HIV infection. The methods comprise administering a solid composition of the present invention to a patient in need thereof. A solid composition of the present invention can be administered either alone, or in combination with one or more other anti-HCV agents, such as those described hereinabove. The specific inhibitory dose for any particular patient will depend upon a variety of factors including the severity of the HCV infection; the activity of the active ingredient(s) in the particular patient; the specific solid composition employed; the age, body weight, general health, sex and diet of the patient; the time of administration and rate of excretion; the duration of the treatment; drugs used in combination or coincidental with Compound $I_A$, $I_B$ or $I_C$; and like factors well known in the medical arts.

In one embodiment, a method of the present invention comprises administering to a patient in need thereof a solid composition of the present invention and at least another anti-HCV agent, wherein said another anti-HCV agent is selected from HCV polymerase inhibitors (e.g., nucleoside or non-nucleoside HCV polymerase inhibitors), HCV protease inhibitors, HCV helicase inhibitors, CD81 inhibitors, cyclophilin inhibitors, internal ribosome entry site inhibitors, or HCV NS5A inhibitors. Preferably, said another anti-HCV agent is an HCV polymerase inhibitor (e.g., nucleoside or non-nucleoside HCV polymerase inhibitor) or an HCV protease inhibitor. Also preferably, said another anti-HCV agent is interferon or ribavirin, or preferably a combination thereof. The interferon preferably is $\alpha$-interferon, and more preferably, pegylated interferon-$\alpha$ such as PEGASYS (peginterferon alfa-2a). The administration of a solid composition of the present invention and another anti-HCV agent(s) can be concurrent or sequential.

The present invention also features use of a solid composition of the present invention for the manufacture of medicaments for the treatment of HCV infection.

It should be understood that the above-described embodiments and the following examples are given by way of illustration, not limitation. Various changes and modifications within the scope of the present invention will become apparent to those skilled in the art from the present description.

Example 1

Compound $I_A$ was formulated using melt-extrusion as well as spray-drying. Both formulations contained 10% Compound $I_A$, 82% copovidone, 2% Vitamin E TPGS, 5% lauroglycol FCC, and 1% Aerosil 200, and were processed further into compressed tablets. Both forms were tested in an accelerated stability test over 4 weeks. The pharmacokinetic study in dogs showed excellent bioavailability of Compound $I_A$.

Example 2

Compound $I_B$ was mixed with Copovidone at drug loading of 10%, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

The solid dispersion showed that Compound $I_B$ was in an amorphous form, as indicated by PLM. These solid dispersions also exhibited rapid dissolution rate in comparison with Compound $I_B$ in neat amorphous state.

Example 3

Compound $I_B$ was mixed with Copovidone and Vitamin E TPGS at drug loading of 10% and 20%, respectively, and dissolved in an organic solvent (e.g. methanol). The solvent was then removed from the system under heat (~40° C.) and vacuum (rotary evaporation or vacuum oven). Solid dispersion of Compound $I_B$ at 10% drug loading level was ground to fine particles using mortar and pestle, and was then characterized by X-ray powder diffraction (PXRD), DSC and TGA, and in vitro dissolution test. The resultant amorphous solid dispersion at 20% drug loading was also characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

Both solid dispersions showed that Compound $I_B$ was in an amorphous form, as indicated by PXRD, DSC or PLM. These solid dispersions exhibited rapid dissolution rate in comparison with Compound $I_B$ in neat amorphous state.

Example 4

Compound $I_B$ was mixed with Copovidone and Tween 80 or Cremophor RH40 at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

All four solid dispersions showed that Compound $I_B$ was in an amorphous form, as indicated by PLM. These solid dispersions also exhibited rapid dissolution rate in comparison with Compound $I_B$ in neat amorphous state.

Example 5

Compound $I_B$ was mixed with Copovidone and Vitamin E TPGS and Lauroglycol FCC at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

Both solid dispersions showed that Compound $I_B$ was in an amorphous form, as indicated by PLM. These solid dispersions also exhibited rapid dissolution rate in comparison with Compound $I_B$ in neat amorphous state.

Example 6

Compound $I_B$ was mixed with Soluplus and Vitamin E TPGS or Tween 80 or Cremophor RH40 at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

All six solid dispersions showed that Compound $I_B$ was in an amorphous form, as indicated by PLM. These solid dispersions also exhibited rapid dissolution rate in comparison with Compound $I_B$ in neat amorphous state.

Example 7

Compound $I_B$ was mixed with Soluplus (a graft copolymer of polyethylene glycol, polyvinyl caprolactam and polyvinyl acetate) and Vitamin E TPGS and Lauroglycol FCC at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_B$ from above amorphous solid dispersions was evaluated in pH 6.8 phosphate buffer by in situ UV dip probe and HPLC assay.

Both solid dispersions showed that Compound $I_B$ was in an amorphous form, as indicated by PLM. These solid dispersions also exhibited rapid dissolution rate in comparison with Compound $I_B$ in neat amorphous state.

Example 8

One solid dispersion formulation was prepared using spray-drying to produce a solid dispersion powder of amorphous Compound $I_B$ within a polymer matrix. The spray dried powder contained 10% by weight of Compound $I_B$, 85% by weight of Copovidone, and 5% by weight of Vitamin E TPGS. Methanol was used as a solvent for spray drying. The spray dried powder was further dried under vacuum to further remove residual solvent. The dried amorphous solid dispersion was characterized by X-ray powder diffraction (PXRD), DSC and TGA.

The solid dispersion showed that Compound $I_B$ was in an amorphous form, as indicated by either PXRD and DSC.

Example 9

Compound $I_C$ was mixed with Copovidone at drug loading of 10%, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_C$ from above amorphous solid dispersions was evaluated in pH 6.8 phosphate buffer by in situ UV dip probe and HPLC assay.

The solid dispersion showed that Compound $I_C$ was in an amorphous form, as indicated by PLM. These solid dispersions also exhibited rapid dissolution rate in comparison with Compound $I_C$ in neat amorphous state.

Example 10

Compound $I_C$ was mixed with Copovidone and Vitamin E TPGS or Tween 80 or Cremophor RH40 at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_C$ from above amorphous solid dispersions was evaluated in pH 6.8 phosphate buffer by in situ UV dip probe and HPLC assay.

All six solid dispersions showed that Compound $I_C$ was in an amorphous form, as indicated by PLM. These solid dispersions also exhibited rapid dissolution rate in comparison with Compound $I_C$ in neat amorphous state.

Example 11

Compound $I_C$ was mixed with Copovidone and Vitamin E TPGS and Lauroglycol FCC at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_C$ from above amorphous solid dispersions was evaluated in pH 6.8 phosphate buffer by in situ UV dip probe and HPLC assay.

Both solid dispersions showed that Compound $I_C$ was in an amorphous form, as indicated by PLM. These solid dispersions also exhibited rapid dissolution rate in comparison with Compound $I_C$ in neat amorphous state.

Example 12

Compound $I_C$ was mixed with Soluplus and Vitamin E TPGS or Tween 80 or Cremophor RH40 at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_C$ from above amorphous solid dispersions was evaluated in pH 6.8 phosphate buffer by in situ UV dip probe and HPLC assay.

All six solid dispersions showed that Compound $I_C$ was in an amorphous form, as indicated by PLM. These solid dispersions also exhibited rapid dissolution rate in comparison with Compound $I_C$ in neat amorphous state.

Example 13

Compound $I_C$ was mixed with Soluplus and Vitamin E TPGS and Lauroglycol FCC at drug loading of 10% and 20%, respectively, and dissolved in an organic solvent (e.g. methanol). The solvent was then removed from the system under heat (~40° C.) and vacuum. The resultant amorphous solid dispersions were characterized by polarized light microscopy (PLM) and in vitro dissolution test. For in-vitro dissolution studies, the release of Compound $I_C$ from above amorphous solid dispersions was evaluated in pH 6.8 phosphate buffer by in situ UV dip probe and HPLC assay.

Both solid dispersions showed that Compound $I_C$ was in an amorphous form, as indicated by PLM. These solid dispersions also exhibited rapid dissolution rate in comparison with Compound $I_C$ in neat amorphous state.

Example 14

Granulation of one formulation containing 15% Compound $I_A$, 7.1% Lauroglycol FCC, 2.9% Vitamin E TPGS and 75% copovidone was performed using a lab mill. Liquid excipients such as Lauroglycol FCC were granulated with the solid raw material, stored in the refrigerator over night for setting and mixed again. The resultant blends were used directly for extrusion. Extrusion was carried out on a small-scale twin-screw extruder (rotation speed of 80 rpm) at a temperature of 140° C. Drug recovery and purity analysis after processing was evaluated by HPLC assay. The solid dispersion was characterized by DSC and polarized light microscopy (PLM). For in-vitro dissolution studies, the release of Compound $I_A$ from above amorphous solid dispersion was evaluated in pH 6.8 phosphate buffer by HPLC assay.

DSC and PLM analysis of the solid dispersion revealed that Compound $I_A$ was in an amorphous form and showed negligible degradation upon processing at high temperature. The solid dispersion exhibited rapid dissolution rate at pH 6.8.

It turned out that Compound $I_A$ can be processed via melt extrusion at temperatures as high as about 170° C., which is far beyond the degradation temperature of the drug substance of around 130° C. without an increase in API degradation.

Example 15

Compound $I_A$ was formulated using melt-extrusion as well as spray-drying. Both formulations included 10% Compound $I_A$, 82% copovidone, 5% Lauroglycol FCC, 2% Vitamin E TPGS, and 1% Aerosil 200. Preparation of the granulate for melt extrusion was performed using a lab mill. Liquid excipients such as Lauroglycol FCC were granulated with the solid raw material, stored in the refrigerator over night for setting and mixed again. The resultant blends were used directly for extrusion. Extrusion was carried out on a small-scale twin-screw extruder (rotation speed of 80 rpm) at a temperature of 150° C. The resultant amorphous solid dispersion was characterized by DSC and polarized light microscopy (PLM). For in-vitro dissolution studies, the release of Compound $I_A$ from above amorphous solid dispersion was evaluated in pH 6.8 phosphate buffer by HPLC assay.

For spray drying, the same composition as applied for melt extrusion was dissolved in a isopropyl alcohol/water mixture, giving a feed solution formulation of 2% Compound $I_A$, 16.4% copovidone, 1% Lauroglycol FCC, 0.4% Vitamin E TPGS, 0.2% Aerosil 200, 70% isopropyl alcohol and 10% DI water. The solid dispersion was manufactured using a lab-scale spray drier at an inlet temperature of 110° C. and a rotavapor for post-drying at 40° C. and 40 mbar abs. to remove remaining solvents. The spray dried solid dispersion was tested for residual solvent content.

The yielded solid dispersions were compressed each into a 100 mg tablet by applying a direct-blend/direct-compression process of 50% solid dispersion, 28% Avicel 102, 14% Di-CAFOS A, 5% croscarmellose sodium, 1% Aerosil 200 and 2% sodium stearyl fumarate.

The pharmacokinetic study in dogs showed excellent bioavailability of Compound $I_A$ in the spray dried as well as in the melt extrusion tablet form compared to in vivo administration of a reference liquid formulation of compound $I_A$. Compressed tablets of both forms exhibited no degradation of compound $I_A$ when stored at 40° C. and 75% rel. humidity over 4 weeks. Dissolution behavior as well as the glass transition temperature remains constant.

Compound $I_A$ was also formulated in solid dispersion with other surfactants such as Tween 80 or Cremophor RH40.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A solid composition comprising
   (1) a compound, or a pharmaceutically acceptable salt thereof, in an amorphous form,
   (2) a pharmaceutically acceptable hydrophilic polymer; and
   (3) optionally a pharmaceutically acceptable surfactant, wherein said compound is selected from the group consisting of:
   methyl[(2S)-1-{(2S)-2-[4-(4-{5-(4-{2-[(2S)-1-{(2S)-2-[(methoxycarbonyl)amino]-3-methylbutanoyl}pyrrolidin-2-yl]-1H-imidazol-4-yl}phenyl)-1-[6-(piperidin-1-yl)pyridin-3-yl]-1H-pyrrol-2-yl}phenyl)-1H-imidazol-2-yl]pyrrolidin-1-yl}-3-methyl-1-oxobutan-2-yl]carbamate (Compound $I_A$), methyl{(2S,3R)-1-[(2S)-2-{6-[(2R,5R)-1-(4-tert-butylphenyl)-5-(2-{(2S)-1-[N-(methoxycarbonyl)-O-methyl-L-threonyl]pyrrolidin-2-yl}-1H-benzimidazol-6-yl)pyrrolidin-2-yl]-1H-benzimidazol-2-yl}pyrrolidin-1-yl]-3-methoxy-1-oxobutan-2-yl}carbamate (Compound $I_B$), and methyl{(2S)-1-[(2S)-2-{5-[(2R,5R)-1-[2,5-difluoro-4-(trifluoromethyl)phenyl]-5-{2-[(2S)-1-{(2S)-2-[(methoxycarbonyl)amino]-3-methylbutanoyl}pyrrolidin-2-yl]-1H-benzimidazol-5-yl}pyrrolidin-2-yl]-1H-benzimidazol-2-yl}pyrrolidin-1-yl]-3-methyl-1-oxobutan-2-yl}carbamate (Compound $I_C$).

2. The composition of claim 1, comprising a solid dispersion which includes:

(1) said compound or salt thereof, and (2) said polymer.

3. The composition of claim 2, wherein said polymer has a $T_g$ of at least 50° C.

4. The composition of claim 3, further comprising said surfactant.

5. The composition of claim 4, wherein said solid dispersion comprises said surfactant.

6. The composition of claim 4, wherein said polymer is a homopolymer or copolymer of N-vinyl pyrrolidone.

7. The composition of claim 4, wherein said polymer is copovidone.

8. The composition of claim 7, wherein said surfactant is D-alpha-tocopheryl polyethylene glycol 1000 succinate.

9. The composition of claim 7, wherein said surfactant is a combination of D-alpha-tocopheryl polyethylene glycol 1000 succinate and propylene glycol monolaurate.

10. The composition of claim 7, wherein said surfactant is sorbitan mono laurate.

11. The composition of claim 4, wherein said solid dispersion is an amorphous solid dispersion.

12. The composition of claim 4, where said solid dispersion is a solid solution which comprises said surfactant.

13. The composition of claim 1, further comprising another anti-hepatitis C virus (HCV) agent.

14. The composition of claim 1, further comprising an HCV protease inhibitor.

15. The composition of claim 1, further comprising an HCV polymerase inhibitor.

16. The composition of claim 4, wherein said compound is Compound $I_A$.

17. The composition of claim 4, wherein said compound is Compound $I_B$.

18. The composition of claim 4, wherein said compound is Compound $I_C$.

19. A process of making the composition of claim 1, comprising dissolving said compound or salt in a solvent.

20. The process of claim 19, wherein said solvent is said polymer.

21. A method of treating HCV comprising administering the composition of claim 1 to a patient in need thereof.

22. The method of claim 21, comprising administering another anti-HCV agent to said patient.

* * * * *